United States Patent
Cawood

(10) Patent No.: US 6,736,803 B2
(45) Date of Patent: *May 18, 2004

(54) URINE BAG AND SELF-RETRACTING DRAIN TUBE THEREFOR

(75) Inventor: C. David Cawood, Houston, TX (US)

(73) Assignee: Cawood Family Limited Partnership, Houston, TX (US)

(*) Notice: Subject to any disclaimer, the term of this patent is extended or adjusted under 35 U.S.C. 154(b) by 0 days.

This patent is subject to a terminal disclaimer.

(21) Appl. No.: 10/242,166

(22) Filed: Sep. 11, 2002

(65) Prior Publication Data

US 2003/0032944 A1 Feb. 13, 2003

Related U.S. Application Data

(63) Continuation-in-part of application No. 09/499,841, filed on Feb. 7, 2000, now Pat. No. 6,471,680, which is a continuation-in-part of application No. 09/229,799, filed on Jan. 13, 1999, now Pat. No. 6,045,542.

(51) Int. Cl.$^7$ .............................. A61M 1/00; A61F 5/44
(52) U.S. Cl. .................................... 604/327; 604/349
(58) Field of Search ..................... 604/322, 324, 604/327, 328, 329, 345, 349, 512, 544; 128/DIG. 24

(56) References Cited

U.S. PATENT DOCUMENTS

| | | | | |
|---|---|---|---|---|
| 3,897,785 A | | 8/1975 | Barto | |
| 4,224,610 A | * | 9/1980 | Quinby | 604/318 |
| 4,306,976 A | * | 12/1981 | Bazzato | 604/328 |
| 4,449,971 A | | 5/1984 | Cawood | |
| 4,581,763 A | * | 4/1986 | Olsen | 604/323 |
| 5,234,420 A | * | 8/1993 | Horton et al. | 604/345 |
| 5,496,300 A | * | 3/1996 | Hirsch et al. | 604/327 |
| 5,531,724 A | * | 7/1996 | Young et al. | 604/327 |
| 6,045,542 A | * | 4/2000 | Cawood | 604/327 |
| 6,471,680 B1 | * | 10/2002 | Cawood | 604/327 |

* cited by examiner

Primary Examiner—Brian L. Casler
Assistant Examiner—Matthew F DeSanto
(74) Attorney, Agent, or Firm—Gary L. Bush; Andrews Kurth LLP

(57) ABSTRACT

This bag includes an improvement in the form of an extendable drain tube that is normally retracted and retained in flat coiled condition against the front wall of the bag. The tube is biased into its coiled condition by the elastic memory of the thermoplastic material from which it is formed and, in a preferred embodiment, the flat coil is oval-shaped with its major axis extending generally vertically when the bag is worn. A retention strap attached to the front wall of the bag serves to hold the drain tube in its coiled condition against the bag's front wall. A valve is located at a distal end of the drain tube, which is used to control drainage. The location of the valve prevents spillage of residual urine upon recoil of the drain tube.

17 Claims, 2 Drawing Sheets

URINE BAG AND SELF-RETRACTING DRAIN TUBE THEREFOR

CROSS REFERENCE TO RELATED APPLICATION

This application is a Continuation-in-Part of application Ser. No. 09/499,841, filed Feb. 7, 2000 now U.S. Pat. No. 6,471,680, which in turn was a continuation-in-part of application Ser. No. 09/229,799, filed Jan. 13, 1999, now U.S. Pat. No. 6,045,542, issued Apr. 4, 2000.

BACKGROUND OF THE INVENTION

Conventional urinary drainage bags are commonly strapped to a patient's leg above the knee, as disclosed in Barto U.S. Pat. No. 3,897,785, so that urine will flow into the bag under the influence of gravity. For an ambulatory patient, such an arrangement is often inconvenient and uncomfortable because, as such a bag becomes filled with urine, there is a tendency for it to slide downwardly along the leg unless additional means are provided on the bag to restrain such sliding movement. Also, such leg bags may be conspicuous through clothing as the bags become filled and may be awkward to drain.

Cawood U.S. Pat. No. 4,449,971 discloses that gravity flow is not essential for purposes of filling a urine collection bag. Intrinsic bladder detrusor muscle tone and intraperitoneal pressures exerted upon the bladder of a catheterized ambulatory patient will cause urine to flow from the bladder to a level as high as 10 centimeters or more above the distal tip of the catheter. A highly effective urinary drainage system may therefore be provided for an ambulatory patient in which the collection bag is carried by a waistband or belt and is worn over the patient's abdomen instead of on the leg.

The bag disclosed in the Cawood patent has a short valve-equipped drain tube that extends downwardly from the bag when the contents are to be drained and that may be folded upwardly and inserted into a pocket provided by the bag when the drain tube is not in use. While such a drain tube may work satisfactorily for an ambulatory patient who is capable of standing with a urine collection bag positioned above a toilet bowl, and then manipulating the drain valve so that the contents of the bag may flow by gravity into the bowl, such a procedure may be difficult if not impossible for patients who are confined to wheelchairs. Such a patient must either try to stand—a maneuver that may involve considerable risk—or must unbuckle the waist strap so that the bag may be held over the toilet bowl and drained.

A main aspect of this invention therefore lies in providing a urine collection bag of the type disclosed in U.S. Pat. No. 4,449,971 with an extendable and retractable drainage tube that allows the contents of such a bag to be drained into a toilet bowl even by a patient confined to a wheelchair and without first requiring removal of the bag by the patient. Specifically, the improvement takes the form of an elongated flexible plastic drainage tube that is in the shape of a flat coil, preferably of oval outline, and is either permanently connected, or detachably connectable, to the drainage port of the urine collection bag, which may be a valved port. The drain tube is permanently attached to the bag drainage port, or in another embodiment, may be detachably joined to a valve provided at that drainage port, depending on the patient's particular needs. For example, wheelchair-bound and otherwise disabled or paralyzed patients may prefer the convenience of having an extension tube permanently connected to their collection bag. However, more ambulatory patients may have only occasional need for an extension tube, such as for night use only, and would prefer a detachable model so as not to have to carry the extra weight and bulk of the drainage tube.

The tube is of soft, flexible thermoplastic material and is thermoformed so that it is biased to assume its flattened coiled shape in the absence of forces applied to extend it. In its coiled condition, the drain tube lies flat against the front wall of the pouch and is held in that position by a retention strap which traverses the front wall of the pouch.

Another advantage of the present construction is that it facilitates use by patients with high urine volume output at night. The elongated drainage tube may be uncoiled and directed into a bedside receptacle, thus allowing a patient to wear an abdominal bag throughout the night without the risks of contamination that might arise if the abdominal bag had to be removed and replaced by other drainage means for nighttime use. In earlier standard practice, a bedside bag would be used at night, and replaced with a leg bag during the day, which exposes the system to non-native bacteria (i.e., bacteria that are not the patient's own), risking clinical infection. Similarly, the elongated drain tube allows a patient to wear an abdominal bag even while undergoing a surgical operation, since urine draining from the bag allows urine output to be monitored by an anesthesiologist. Upon completion of the operation, the drain tube may be disconnected from the bedside receptacle, allowed to return to its coiled condition, and replaced under the retaining strap of the abdominal bag, thus restoring the abdominal bag to its original condition for inpatient or outpatient use.

The drain tube is provided at its distal end with a valve to control drainage. By having the valve located at the distal end of the drain tube, the patient is assured that, when the valve is closed, there will be no spillage of any residual droplets of urine left in the drain tube upon recoiling the tube to its original condition.

Other features, objects, and advantages of the invention will become apparent from the specification and drawings.

IN THE DRAWINGS

DETAILED DESCRIPTION OF THE PREFERRED EMBODIMENT OF THE INVENTION

Figure 1:
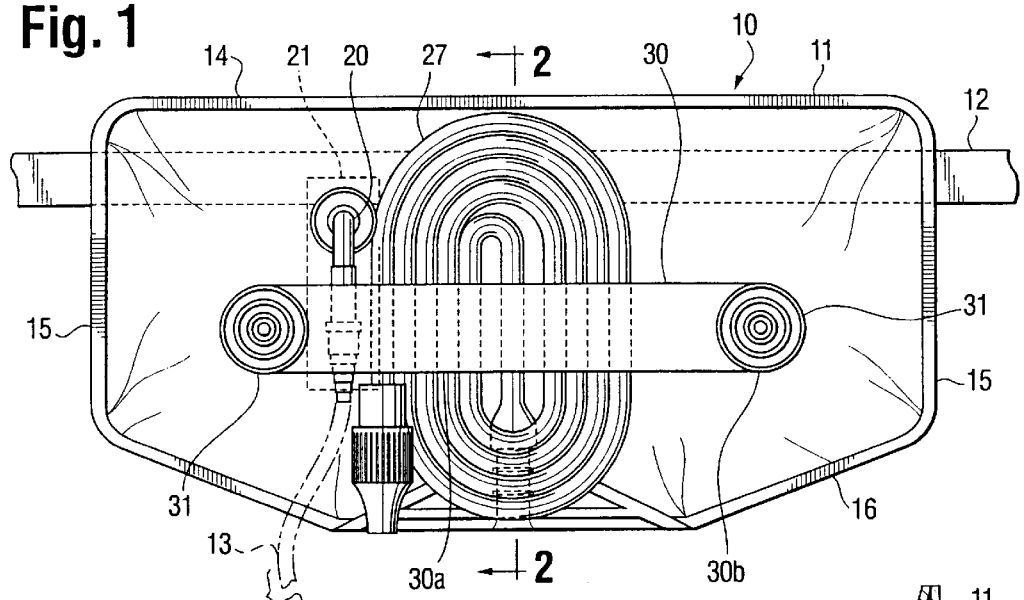
FIG. 1 is a front elevational view of an abdominal bag equipped with the elongated drain tube of this invention.

Referring to the drawings, the numeral 10 generally designates a urine collection device comprising an abdominal bag 11, a belt 12 for supporting the bag about a wearer's waist, and a catheter 13 for conveying urine from the bladder to the collection bag. In use, the bag would be worn as shown and described in aforementioned U.S. Pat. No. 4,449,971, the disclosure of which is incorporated by reference herein.

The bag 11 is substantially flat when empty and is dimensioned to extend over a patient's abdomen or belly.

The front and rear walls 11a and 11b of the bag are joined together along their top, side and bottom edges 14, 15 and 16, respectively. Top edge 14 is generally straight and extends horizontally when the bag is worn. The walls of the bag may be formed of any suitable thermoplastic film that is tough, flexible, and liquid/gas impermeable. As indicated in the drawings, the edges 14–16 are preferably heat sealed together. The bottom edge 16 is generally V-shaped in outline with its side sections sloping downwardly toward the bag's vertical midline 17.

The bag may optionally include a soft, flexible rear panel 11c which may be of flocked or non-woven fabric. Such a rear panel, when provided, serves as a comfort panel to keep the bag from sticking to a patient's skin, and would preferably be joined to the rear wall 11b by the same peripheral heat seal extending along edges 14–16. Belt 12 may be secured to rear wall 11b by any suitable means. Where a rear comfort panel 11c is provided, the strap portions 12a of the belt may extend outwardly through vertical slits (not shown) in the rear comfort panel, in which case direct attachment of the belt to the rear wall 11b becomes unnecessary since the rear comfort panel then serves to join the belt and bag together. Such a comfort panel is disclosed in commonly owned U.S. Pat. No. 6,045,542, issued Apr. 4, 2000, the disclosure of which is incorporated by reference herein.

An inlet tube 20 formed of polyvinyl chloride or other suitable thermoplastic material is heat sealed to the upper front wall 11a of the bag and communicates in the interior of the bag with a suitable one-way valve 21. As shown in FIG. 1, the exterior portion of the inlet tube is operatively permanently connected to a standard catheter adapter, to which is connected the proximal end 13a of catheter 13. The connection is a not a permanent one, but rather, is preferably a separable connection so as to facilitate changing the catheter without having to change the collection bag, or vice-versa, in the event of malfunction of either the catheter or the collection bag.

The one-way valve 21 may be formed of a pair of flexible thermoplastic strips heat sealed along their edges to define a passage communicating at one end with inlet tube 20 and open at its other end only when fluid pressure within the passage forces the strips apart, thereby functioning as an anti-refluxing flap valve as disclosed more fully in aforementioned U.S. Pat. No. 4,449,971.

Figure 3:
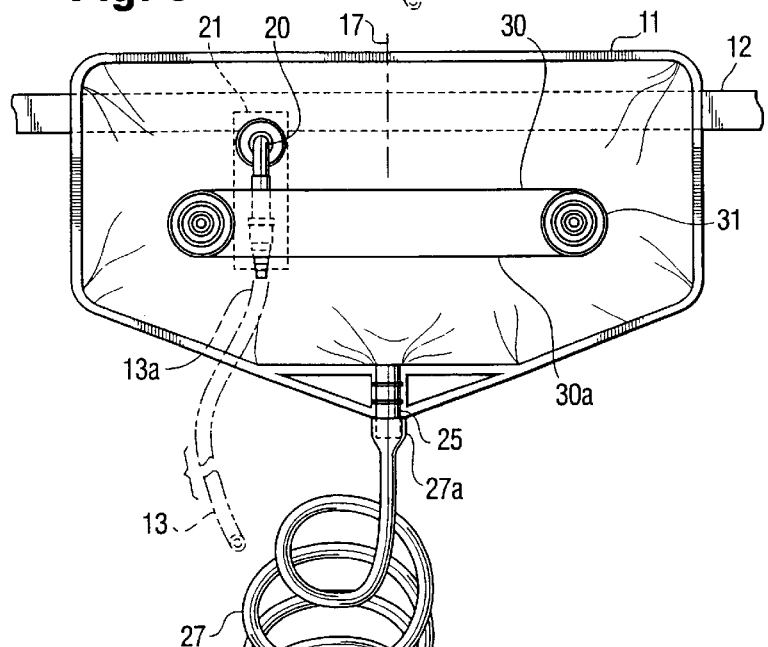
FIG. 3 is a front elevational view similar to FIG. 1 but showing the drainage tube in partially uncoiled condition.
Figure 5:
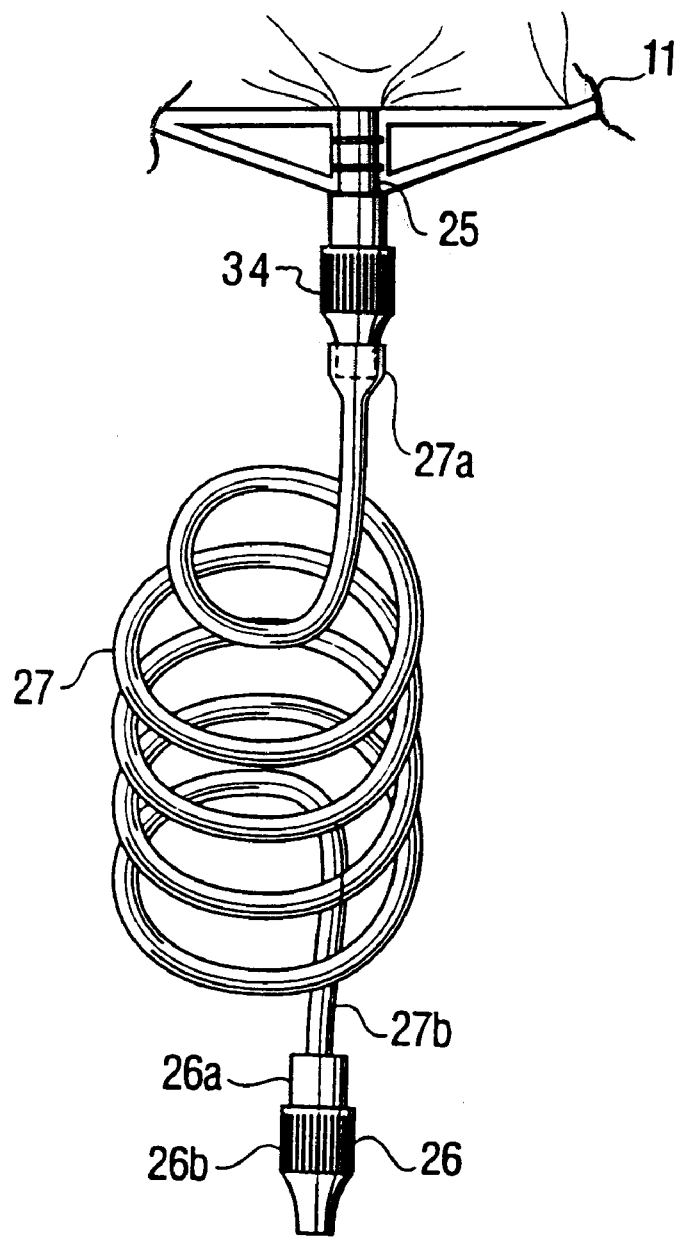
FIG. 5 is a front elevational view similar to FIG. 3, partially broken away, showing an alternate embodiment in which the drainage tube is detachable from the collection bag by way of a valve provided at the drainage port of the collection bag.

A tubular drain port 25 is heat sealed to the lower edges of the bag and communicates with the bag's interior. A valve 34 may be provided at the tubular drain port 25, as shown in FIG. 5, with a self-retracting flexible train tube 27 detachably secured thereto. In the embodiment shown in FIG. 5, a second valve 26 may also be provided at the opposite (distal) end 27b of a self-retracting flexible drain tube 27. Removable attachment of the flexible drain tube 27 to the tubular drain port 25 is achieved by stretching the proximal end 27a over the tip of the valve 34 attached to the valve drain port 25 extending below the bottom edge 16 of the bag 11. Alternatively, as best shown in FIG. 3, the valve 26 may be provided only at the opposite (distal) end 27b of a self-retracting flexible drain tube 27 permanently attached at its proximal end 27a to the tubular drain port 25.

The particular valve 26 depicted in the drawings is composed of two elements 26a and 26b that are threadedly connected to each other. Opening and closing of the valve 26 is achieved simply by rotating element 26b one way or the other with respect to element 26a. Since such a valve 26 is entirely conventional and well known for use in collection appliances, a more detailed description of its structure and operation is believed unnecessary. The structure of valve 34 is identical.

Figure 2:
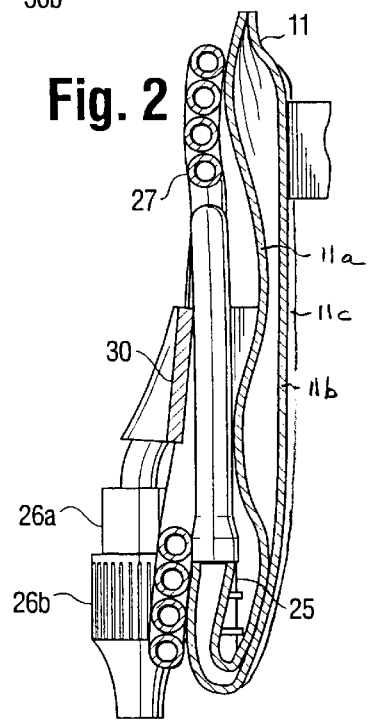
FIG. 2 is an enlarged vertical sectional view taken along line 2—2 of FIG. 1.

The tubular drain port 25 is located along the bag's vertical midline as shown in FIGS. 1 and 2. In the permanently attached version, the flexible self-retracting drain tube 27 has its proximal end connected to the valved drain port 25, and its distal end connected to the valve 26. In the detachable version, the connection of the self-retracting drain tube 27 to the valve 26 is detachable. Detachability is achieved by securably inserting the proximal tubing end 27a, for example with a press fit, into the outlet end of valve element 34b. Detachability of the self-retracting drain tube 27 to the valve 34 allows bag 11 to be used in the manner already described in the aforementioned U.S. Pat. No. 4,449,971 when the use of an elongated self-retracting drainage tube is deemed inconvenient or unnecessary.

The location of the valve 26 at the distal end 27b of the self-retracting drain tube 27 is found to be advantageous over having the valve 26 located at the proximate end 27a. This is because in use, when the valve 26 is located at the proximate end 27a and attached to the tubular drain port 25, the self-retracting drain tube 27 may, upon recoil, tend to expel any urine remaining in the tubing out the open distal end 27b of the drain tube 27. By having the valve 26 located at the distal end 27b, the patient can simply close the valve 26 after drainage into a toilet 33, then allow the self-retracting drain tube 27 to recoil without concern over spillage of any residual droplets of urine in the drain tube 27, inasmuch as the closed valve 26 would prevent such residual urine from leaking out the distal end 27b. At worst, the residual urine in the coiled drain tube 27 could creep back into the tubular drain port 25, but it would simply re-enter the bag 11 for drainage at a later time.

Another benefit of locating the valve 26 at the distal end 27b of the self-retracting drain tube is that if the patient's mobility is confined and the patient is unable to manipulate the valve 26 himself or herself, an assistant charged with the task of draining the bag 11 on the patient's behalf can open the valve 26 at a location separated from the patient, even behind a curtain if desired, in order to better protect the patient's privacy.

Figure 4:
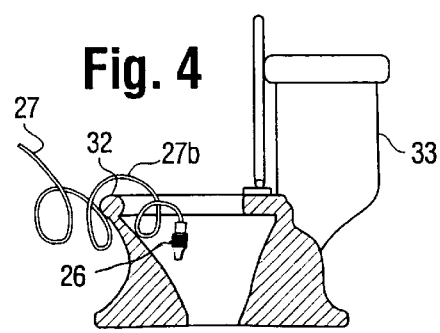
FIG. 4 is a diagramatic view illustrating how the coiled drainage tube may be hooked over the rim of a flush toilet.

The drain tube 27 is formed from a soft, flexible, thermoplastic material that may be thermoformed into a flat, coiled shape and will be biased to retain that shape, or retract into it, because of its elastic memory. Polyvinyl chloride is believed particularly effective, preferably of a durometer value on the Shore A scale of about 65 to 80, but other thermoplastic materials having similar properties may also be used. It has been found that if a PVC tube having an inside diameter of ¼ inches and a length of 18–24 inches is coiled into a flat spiral, preferably one of oval shape as shown in FIG. 1, and is then heated for approximately 15 minutes at a temperature of 200 to 225° F., the tubing when cooled will have acquired a "set" and will tend to return to its coiled configuration when it is extended and then released. Such temperatures are commonly encountered in gas (e.g., ethylene oxide) sterilization processes, so a separate manufacturing step can advantageously be avoided. Indeed, it has been found that simply placing the coil in a paper sleeve will allow it to "set" in the desired configuration during such gas sterilization. Thus, the drainage tube may be easily extended for drainage of bag 11 as indicated in FIGS. 3 and 4 and, when the forces of extension are removed, the elastic memory will cause, or at least contribute, to self-retraction of the tube into the coiled configuration depicted in FIGS. 1 and 2. In that flat coiled shape, preferably with the long axis of the oval extending vertically when the bag is supported as shown in FIG. 1, the coiled tube may be folded upwardly against the front face 11a of bag 11.

Retention means are provided by the bag to hold the coiled tube 27 in its retracted condition. In the illustration given, the retention means takes the form of a flexible strap 30. The elongated strap extends transversely (horizontally) and includes central portion 30a and end portions 30b. Circular heat seals 31 not only join the end portions 30b to the front wall of the bag but also secure together the front and rear walls 11a and 11b at two laterally-spaced zones of attachment. It will be observed that the two spots or zones of interconnection are spaced equal distances on opposite sides of the vertical midline of the bag and that each heat seal 31 is located approximately midway between that midline and a side edge 15. The strap 30 is located so that when the drain tube 27 is coiled and folded upwardly into raised position the valve and the center of the flat coil will be at approximately the same elevation as the strap and can be easily tucked between front wall 11a and the central portion 30a of the strap (FIGS. 1 and 2).

As indicated in FIG. 3, the thermoformed drain tube 27 tends to retain its coiled condition even when its distal end 27b is pulled or extended outwardly away from the bag 11 during a draining procedure. That tendency to remain in coiled condition has been found useful in helping a user temporarily affix the distal end to a toilet bowl in preparing for a draining operation. FIG. 4 illustrates how the coils at the distal end 27b of drain tube 27 may be looped or hooked over the edge 32 of the bowl of a conventional flush toilet 33 by a patient seated in a wheelchair (not shown), thereby allowing the patient or assistant to use both hands in manipulating valve 26.

While in the foregoing, an embodiment of the invention has been described in detail for purposes of illustration, it will be understood by those skilled in the art that many of these details may be varied without departing from the spirit and scope of the invention.

I claim:

1. A urine collection device comprising a flat bag adapted to be worn by a patient across the abdomen, said bag having front and rear walls of flexible thermoplastic joined to each other along top, bottom, and side edges to define a urine-receiving chamber; support means for supporting said bag from a patient's waist; a drain port located along said bottom edge and communicating with the interior of said bag; an inlet tube joined to said front wall above said drain port and adapted to be connected to a urethral catheter; and a one-way inlet valve communicating with said inlet tube for preventing flow in a reverse direction therethrough; wherein the improvement comprises an elongated flexible thermoplastic drain tube having first and second ends; said first end being connected to said drain port; said drain tube normally assuming a flat coiled condition and biased into said condition by the elastic memory of the thermoplastic material from which said drain tube is formed; retention means provided by said bag for holding said drain tube in flat coiled condition against the front wall of said bag; and a manually operable valve being provided at said second end of the drain tube.

2. The device of claim 1 in which said drain tube when in flat coiled condition is oval in outline.

3. The device of claim 2 in which said oval has a long axis extending generally vertically when said bag is worn.

4. The device of claim 1 in which said first end of said drain tube is permanently connected to said drain port.

5. The device of claim 1 in which said retention means comprises a flexible strap traversing a mid section of said front wall of said bag; said strap having a central portion and a pair of opposite end portions; said end portions being secured to said front wall and said central portion extending over said drain tube and holding the same in coiled condition against the front wall of said bag.

6. The device of claim 1 in which said second end of said drain tube is permanently connected to said valve means.

7. The device of claim 1 in which the first end of said drain tube is permanently connected to said drain port.

8. The device of claim 1 in which the second end of said drain tube is permanently connected to said valve means.

9. The device of claim 1 in which the first end of said drain tube is detachably connected to said drain port by a second valve means provided on said drain port.

10. A urine collection device comprising a flat bag adapted to be worn by a patient across the abdomen, said bag having front and rear walls of flexible thermoplastic joined to each other along top, bottom, and side edges to define a urine-receiving chamber; support means for supporting said bag from a patient's waist; a drain port located along said bottom edge and communicating with the interior of said bag; an inlet tube joined to said front wall above said drain port and adapted to be connected to a urethral catheter; and a one-way inlet valve communicating with said inlet tube for preventing flow in a reverse direction therethrough; wherein the improvement comprises an elongated flexible thermoplastic drain tube having first and second ends and being flexible between a normal retracted condition and an extended condition; said first end being connected to said drain port; said drain tube normally assuming a substantially flat coiled condition and being biased into said flat coiled condition by the elastic memory of the thermoplastic material from which said drain tube is formed; a retention device provided by said bag for holding said drain tube in said substantially flat coiled condition against the front wall of said bag; and a manually operable valve being provided at said second end of said drain tube.

11. The urine collection device of claim 10 in which said flat coiled condition of said drain tube is oval in outline.

12. The urine collection device of claim 11 in which said oval has a long axis extending generally vertically when said flat urine collection bag is worn.

13. The urine collection device of claim 10, wherein said first end of the drain tube is removably secured to a drain valve of the flat collection bag.

14. The urine collection device of claim 13, wherein when worn by a patient, said manually operable valve means is controllable from a location spaced away from the patient, to selectively initiate drainage of the urine collection bag and to selectively stop drainage of the urine collection bag.

15. The urine collection device of claim 10, wherein said first end of the drain tube is permanently secured to a drain port of the flat urine collection bag.

16. The urine collection device of claim 10, in which said flat urine collection bag defines a front wall; said retention device comprises a flexible strap traversing a mid section of said front wall of said flat urine collection bag; said strap having a central portion and a pair of opposite end portions; said end portions being secured to said front wall and said central portion extending over said drain tube and holding the same in coiled condition against said front wall of said flat urine collection bag.

17. The urine collection device of claim 10, in which said flat coiled drain tube is defined by substantially concentric coils of progressively larger size from said first end to said second end.

* * * * *